United States Patent [19]

Albrecht et al.

[11] Patent Number: 4,797,498

[45] Date of Patent: Jan. 10, 1989

[54] FLAVONOXYPROPANOLAMINES AND ESTERS OF FLAVONOXYPROPANOLAMINES AS ANTIARRHYTHMIC AGENTS

[75] Inventors: William L. Albrecht; Edwin S. Wu, both of Rochester, N.Y.

[73] Assignee: Pennwalt Corporation, Philadelphia, Pa.

[21] Appl. No.: 887,670

[22] Filed: Jul. 18, 1986

[51] Int. Cl.$^4$ ............................................ C07D 311/30
[52] U.S. Cl. ...................................................... 549/403
[58] Field of Search ........................................... 549/403

[56] References Cited

U.S. PATENT DOCUMENTS

| 4,391,821 | 7/1983 | Korbonits | 514/456 |
| 4,463,176 | 7/1984 | Dennis et al. | 546/208 |
| 4,495,198 | 1/1985 | Wu | 514/456 |
| 4,501,755 | 2/1985 | Wu | 514/456 |
| 4,668,804 | 5/1987 | Wu | 549/403 |
| 4,668,805 | 5/1987 | Wu | 549/403 |

OTHER PUBLICATIONS

Wang et al., Acta Pharm. Sinica, 15, 253(1980).

Primary Examiner—Nicky Chan
Assistant Examiner—Grace Hanks

[57] ABSTRACT

Ester derivatives of N-substituted and N,N-disubstituted aminopropanoloxy flavones in which the aminopropanoloxy side chain is inserted at either the 5-, 6-, 7- or 8-position of the flavone nucleus, and N-substituted and N,N-disubstituted aminopropanoloxy flavones in which the aminopropanoloxy side chain is inserted at the 8-position of the flavone nucleus; useful as anti-dysrhythmic agents.

11 Claims, No Drawings

FLAVONOXYPROPANOLAMINES AND ESTERS OF FLAVONOXYPROPANOLAMINES AS ANTIARRHYTHMIC AGENTS

BACKGROUND OF THE INVENTION

In D. Wang et al, *Acta Pharmaceutica Sinica*, vol. 15, 253 (1980), flavone derivatives in which an alkylaminopropanoloxy side chain is inserted at either the 4′, 5-, 6-, or 7-position of the flavone nucleus were disclosed.

In P. Da Re et al, *Journal of Medicinal Chemistry*, vol. 15, 868 (1972), flavone derivatives in which an alkylaminopropanoloxy side chain is inserted at either the 6- or 7-position of the flavone nucleus, and a methyl group is also inserted at the 3-position of the flavone nucleus, were disclosed.

U.S. Pat. No. 4,391,821 dated July 5, 1983, claimed various benzopyran derivatives in which an alkylaminopropanoloxy side chain is inserted at the 7-position of the benzopyran nucleus and disclosed that the derivatives were useful in treatment of heart disease.

The above-mentioned publications and patent did not disclose benzopyran derivatives with either ester derivatives of the propanoloxy side chain or a side chain substituted at the 8-position.

BRIEF SUMMARY OF THE INVENTION

The invention is a compound of formula I

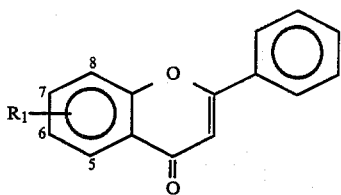

(I)

wherein
$R_1$ is

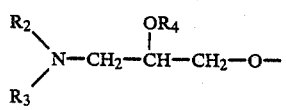

$R_2$ is lower alkyl,
$R_3$ is H or benzyl,
$R_4$ is H, lower alkanoyl, naphthoyl, benzoyl, substituted benzoyl, phenylalkanoyl, substituted phenylalkanoyl, diphenyl alkanoyl, or substituted diphenylalkanoyl, and the numbers 5, 6, 7, and 8 denote the 5-, 6-, 7-, and 8-positions of the flavone nucleus, respectively, provided that (1) $R_1$ is substituted at either the 5-position, 6-position, 7-position or 8-position of the flavone nucleus when $R_4$ is not H, (2) $R_1$ is substituted at the 8-position of the flavone nucleus when $R_4$ is H, (3) $R_3$ is H when $R_4$ is H, (4) $R_2$ is not t-butyl when $R_1$ is substituted at the 5-position, 6-position, or 7-position of the flavone nucleus, (5) $R_4$ is not lower alkanoyl when $R_1$ is substituted at the 5-position, 6-position, or 7-position of the flavone nucleus, and (6) $R_4$ is not benzoyl and substituted benzoyl when $R_1$ is substituted at the 7-position and $R_2$ is n-propyl.

The compounds of this invention have antiarrhythmic activity.

This invention also includes a method for administering a compound of formula I to a mammal with dysrhythmia. In addition, it includes processes for making the compounds of formula I.

DETAILED DESCRIPTION

Definitions

"Lower alkyl" is alkyl of 1 to 6 carbon atoms.

"Lower alkanoyl" is alkanoyl of 1 to 6 carbon atoms, including the carbonyl carbon.

"Lower alkoxy" is alkoxy of 1 to 6 carbon atoms.

"Substituted benzoyl" is benzoyl in which the phenyl moiety is mono- or di-substituted with lower alkyl, lower alkoxy, or halogen such that the substituents may be chosen independently of each other in a disubstituted moiety. The halogen can be either chlorine, fluorine, bromine or iodine.

"Substituted phenylalkanoyl" and "substituted diphenylalkanoyl" are phenylalkanoyl and diphenylalkanoyl, respectively, in which the phenyl moiety is either unsubstituted or mono- or di-substituted with lower alkyl, lower alkoxy, or halogen such that the substituents may be chosen independently of each other in the disubstituted phenyl moiety.

The alkanoyl moiety of phenylalkanoyl or diphenylalkanoyl contains 2 to 4 carbon atoms. The number of alkanoyl carbon atoms includes the carbonyl carbon atom.

Diphenylalkanoyl is either α,α-diphenylacetyl, or β,β-diphenylpropanoyl.

Subgeneric aspects of the invention include those in which the invention is a compound of formula I as defined above except that either:

(1) $R_1$ is substituted at the 8-position of the flavone nucleus;

(2) $R_1$ is substituted at the 7-position of the flavone nucleus;

(3) $R_4$ is limited to lower alkanoyl, naphthoyl, benzoyl, phenylalkanoyl, and diphenylalkanoyl;

(4) $R_4$ is limited to lower alkanoyl, naphthoyl, benzoyl, phenylalkanoyl and diphenylalkanoyl, and $R_1$ is substituted at the 8-position of the flavone nucleus, or (5) $R_4$ is limited to lower alkanoyl, naphthoyl, benzoyl, phenylalkanoyl and diphenylalkanoyl, and $R_1$ is substituted at the 7-position of the flavone nucleus.

Formation of the Compounds:

General scheme and the limitation to one side chain

Methods A through E, described below, provide procedures for proceeding from a hydroxyflavone of the formula

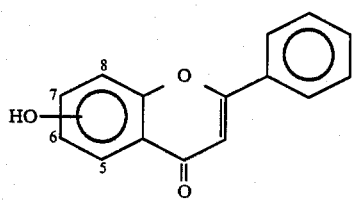

in which the OH group is either at the 5-, 6-, 7- or 8-position of the flavone nucleus, to the compounds of the invention.

Methods A through E are summarized in Chart A below. In Chart A, Bz means benzyl.

If the hydroxyl group is substituted at the 8-position of the flavone nucleus in the starting compound for Method A, the propoxy side chain will also be at the 8-position in other compounds subsequently generated by Methods B, C, D or E. Similarly, substitution of the hydroxyl group at the 5-, 6-, or 7-position results in substitution of the propoxy groups at the 5-, 6-, or 7-position, respectively.

The compounds formed by Method B, Variation 1 are novel and also constitute and invention.

In chart A, $R_2$ is lower alkyl and $R_4$ is lower alkanoyl, naphthoyl, benzoyl, substituted benzoyl, phenylalkanoyl, substituted phenylalkanoyl, diphenylalkanoyl or substituted diphenylalkanoyl, except that, in method E, $R_2$ is t-butyl.

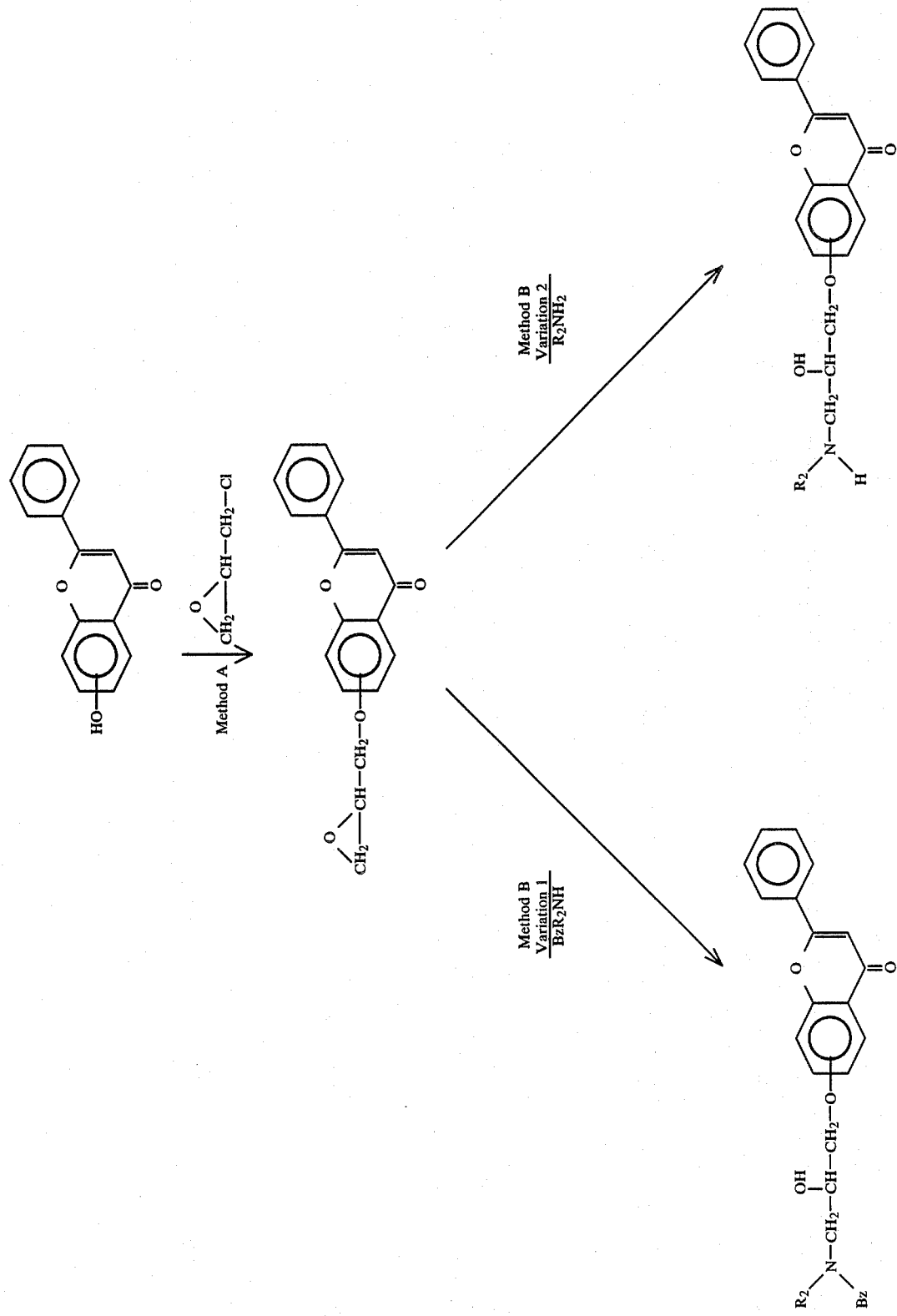

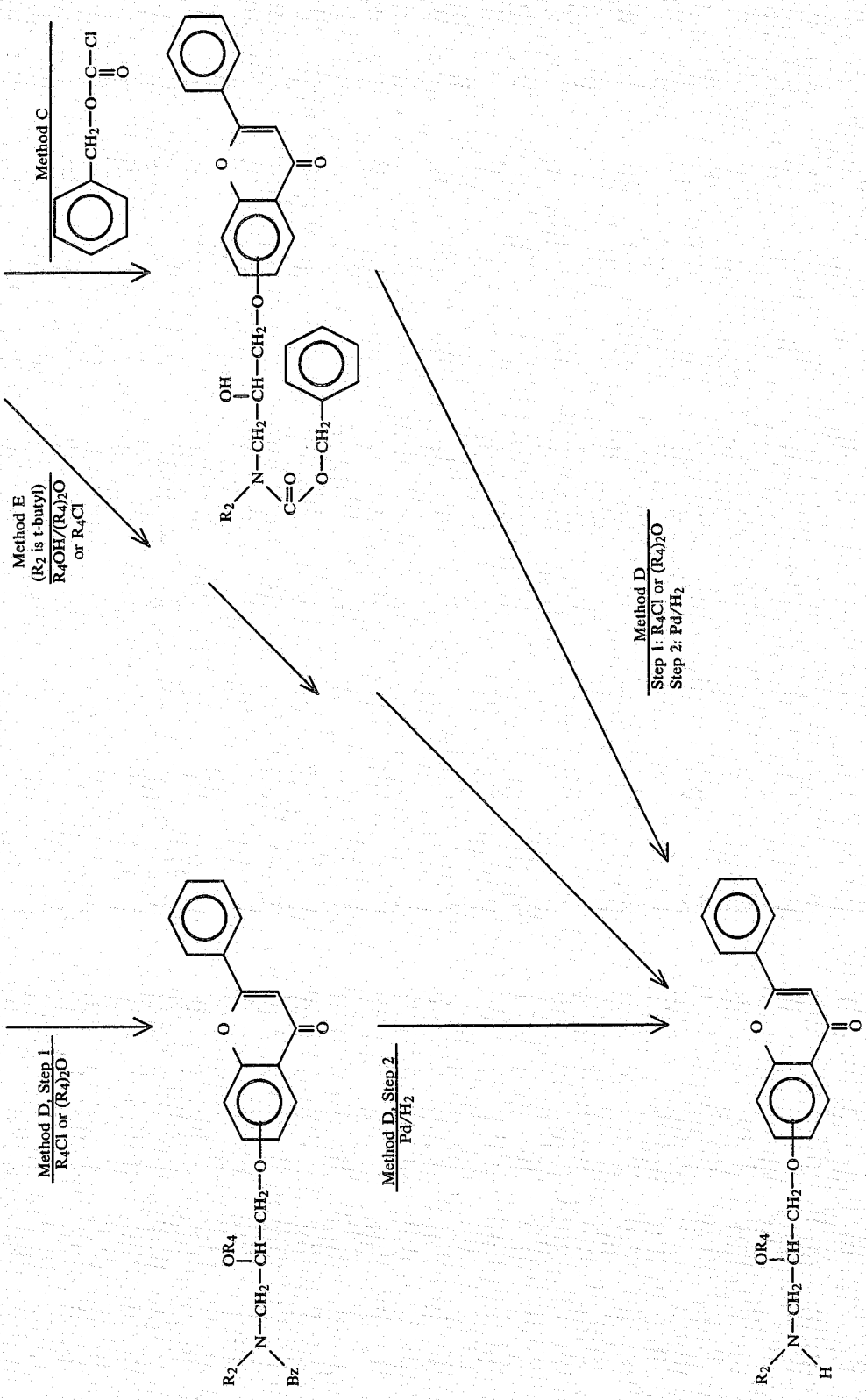

Illustrative Examples:

In the following Examples, the phrase "title compound" refers to the compound in the title of the paragraph in which that phrase is used.

For brevity, t-butyl means tertiary butyl, TLC means thin layer chromatography, HPLC means high pressure liquid chromatography, 10% Pd/C means a catalyst composition of Pd (10% by weight) on carbon, abs means absolute, MeOH means methanol, EtOH means ethanol, EtAc means ethyl acetate, i-PrOH means isopropyl alcohol, i.v. means intravenous, and aq means aqueous.

EXAMPLE 1

Preparation of
7-[2-(diphenylacetoxy)-3-(propylamino)propoxy]flavone hydrochloride 7-(2,3-Epoxypropoxy)flavone (Method A)

To a solution of 82.2 g (2.06 mol) of sodium hydroxide in 585 ml of water were added 3.7 liters of isopropanol and then 490 g (2.06 mol) of 7-hydroxyflavone. To the above mixture were then added 1645 ml (20.5 mol) of epichlorohydrin and the mixture was heated at 70° for 2 hr with stirring. The hot reaction mixture was filtered to remove a solid dimeric by-product. The filtrate was concentrated under reduced pressure (water aspirator) at 50° to 60°. The semisolid residue was treated with 4.4 liters of refluxing isopropanol and more of the dimer from the hot mixture. The clear filtrate on cooling yielded a solid. This was filtered, washed with 600 ml of isopropanol and air dried; yield 434.3 g (72%) of a tan-colored product, m.p. 123°–130° (a pure sample of the title compound melts at 133°–135°.)

7-[2-hydroxy-3-(propylamino)propoxy]flavone
(Method B, Variation 2)

To 10.35 liters (125.9 mol) of n-propylamine were added 530 g (1.8 mol) of 7-(2,3-epoxypropoxy)flavone and 5.4 liters of abs ethanol. The mixture was heated at 50° to 55° for 1.5 hr, with stirring. The reaction mixture was cooled and clarified by filtration, and the filtrate concentrated in a rotary evaporator to a volume of 4.0 liters. The resulting solid product was filtered and washed with 1 liter abs ethanol; yield 383 g (60%) of a bright yellow solid, m.p. 144°–146°. The bright yellow solid was suspended in a mixture of 3.41 liters of water and 1.14 liters of 95% ethanol and then treated with 537 ml of 2.5N hydrochloric acid to obtain a solution of pH 1 to 2. The resulting aqueous solution was extracted twice with 537 ml of methylene chloride and then four times with 268 ml of $CH_2Cl_2$. The aqueous solution was clarified by filtration. Water (1.14 liters) was added to the filtrate, followed by the slow addition of 537 ml of 2.5N NaOH until the mixture tested for a pH of 10 to 11 to give a solid precipitate. The mixture was stirred for ½ hr. The product was filtered, washed with 2.68 liters water and air dried; yield, 362 g (57%) of the title compound as a pale yellow powder, m.p. 145°–147°.

7-[2-Hydroxy-3-[N-(benzyloxycarbonyl)-propylamino]-propoxy]flavone (Method C)

Triethylamine (6.07 g, 60 mmol) was added slowly to a suspension of 5.08 g (15 mmol) of 7-[2-hydroxy-3-(propylamino)propoxy]flavone and benzylchloroformate (2.69 g, 15 mmol) in 100 ml of methylene chloride. The resulting solution was refluxed for 4 hr. The white solid was removed by filtration; the filtrate was diluted with $CH_2Cl_2$(150 ml), washed with 5% aq. HCl several times, in order to remove trace amounts of amine, and dried ($Na_2SO_4$). Evaporation of the solvent gave a tan viscous liquid which solidified upon addition of ether. Recrystallization of the solid (6.68 g) from EtAc-hexane afforded 3.70 g (52% yield) of the title compound as a white crystal, mp 92°–94° C.

7-[2-(Diphenylacetoxy)-3-[N-(benzyloxycarbonyl)-propylamino]propoxy]flavone (Method D, Step 1)

A mixture of 7-[2-hydroxy-3-[N-(benzyloxycarbonyl)-propylamino]propoxy]flavone in crude form (5.09 g, 11 mmol), diphenylacetyl chloride (10.20 g, 44 mmol), and triethylamine (19.0 ml, 136 mmol) in toluene (65 ml) was refluxed under nitrogen for 18 hr. Toluene was removed by evaporation and the oily residue was dissolved in chloroform, washed twice with saturated $NaHCO_3$ and once with water, and then dried ($K_2CO_3$). The dried solution, upon evaporation, gave a brown oil which was purified by HPLC (Water Associates PrepLC/Systems 500) using 3% acetone/$CH_2Cl_2$ that contained a small amount of $NH_4OH$. A tan syrup of the title compound was obtained; 5.57 g (76% yield).

7-[(2-Diphenylacetoxy-3-(propylamio)prpoxy]flavone hydrochloride (Method D, Step 2)

Diphenylacetate (5.5 g, 8.2 mmol) was dissolved in a solvent consisting of 100 ml of abs. ethanol and 100 ml of glacial acetic acid with gentle warming on a steam bath, and 0.2 g of 10% Pd/C was added in the presence of nitrogen. The mixture, in a pressure bottle, was then placed on the Paar apparatus. Hydrogenation was slow, so additional 0.5 g of 10% Pd/C was added after 4 hr. and the reaction continued until the theoretical amount of hydrogen was taken up. The reaction mixture was filtered through a glass-wool filter paper and the filtrate was evaporated to give a yellow syrup (4.15 g) which was dissolved in chloroform, washed twice with saturated $NaHCO_3$ and once with water, and dried ($MgSO_4$). The dried solution was evaporated and the residue thus obtained was dissolved in hot isopropyl alcohol, acidified with HCl/EtOH, and mixed with anhydrous ether, to give 1.0 g (21% yield) of the title compound as a white solid, mp 193.5°–195.5° C.

EXAMPLE 2

Preparation of
8-[2-(benzoyloxy)-3-(isopropylamino)propoxy]flavone hydrochloride 8-(2,3-Epoxypropoxy)flavone (Method A)

8-Hydroxyflavone (17.9 g, 75 mmol) (see Awad et al, J. Org. Chem., 25, 1333 (1960)) was suspended in a solvent consisting of 22 ml of water and 135 ml of isopropanol. Epichlorohydrin (59 ml, 75 mmol) and NaOH (3.0 g, 75 mmol) were added and the reaction mixture was heated at 70° C. for 3½ hours. The reaction mixture was then cooled and filtered, and the solvent was removed under reduced pressure. The residue was taken up in 600 ml of $CH_2Cl_2$, washed twice with 600 ml of $H_2O$, dried and the remaining solvent was removed by evaporation. This gave 21.9 g of light tan solid (99% yield). The product was used in the next step without further purification.

8-[2-Hydroxy-3-(benzylisopropylamio)propoxy]flavone hydrochloride (Method B, Variation 1)

A suspension of 8-(2,3-epoxypropoxy)flavone (5.09 g, 16.5 mmol), N-isopropyl-benzylamine (3.6 ml, 19.8 mmol), and isopropanol (100 ml) was placed under $N_2$ and heated at 70° C. (oil bath temperature) for 18 hr. Isopropanol was removed in a rotary evaporator. The residue was dissolved in abs ethanol by heating in a steam bath and acidified with dry HCl in EtOH. A white precipitate of the title compound was formed upon standing, collected, and washed with cold EtOH; 5.75 g (73% yield).

8-[2-(Benzoyloxy)-3-(benzylisopropylamino)propoxy]-flavone hydrochloride (Method D)

Using the procedure described in Example 1 for Method D, step 1, but substituting 8-[2-hydroxy-3-(benzylisopropylaminio)propoxy]flavone hydrochloride for 7-[2-hydroxy-3-[N-(benzyloxycarbonyl)-propylamino]-propoxy]flavone and substituting benzoyl chloride for diphenylacetyl chloride, the free base, 8-[2-benzoyl-3-(benzylisopropylamino)propoxy]flavone, was produced. The free base was converted into the title compound by treatment with HCl in EtOH. (overall yield, 80% based on the tertiary amine.)

8-[2-(Benzoyloxy)-3-(isopropylamino)propoxy]flavone hydrochloride

Using the procedure described in Example 1 for Method D, step 2, but substituting 8-[2-(benzoyloxy)-3-(benzylisopropylamino)propoxy]flavone hydrochloride for 7-[2-(diphenylacetoxy)-3-[N-(benzyloxycarbonyl)-propylamino]propoxy]flavone, the title compound was obtained in 73% yield. m.p. 238°-240° C.

EXAMPLE 3

Preparation of 8-[2-hydroxy-3-(t-butylamino)propoxy]flavone hydrochloride

Following variation 2 of Method B, as outlined in Example 1, but substituting t-butylamine for n-propylamine and 8-(2,3-epoxypropoxy)flavone for 7-(2,3-epoxypropoxy)flavone, the title compound was prepared in 58% yield m.p. 243°-245° C. (EtOH).

EXAMPLE 4

Preparation of 8-[2-(Benzoyloxy)-3-(t-butylamino)propoxy]flavone hydrochloride(Method E)

The compound, 8-[2-hydroxy-3-(t-butylamino)-propoxy]flavone (0.5 g, 1.36 mmol), was combined with benzoic acid (2.65 g, 21.8 mmol) and benzoic anhydride (0.37 g, 1.63 mmol) in 5.4 ml of anhydrous HMPA. The reaction was stirred at room temperature under $N_2$ for 24 hours. At that point, no starting hydroxy compound was detected by TLC. The reaction was poured into 20 ml of $H_2O$ and the pH was adjusted to 8 with concentrated $NH_4OH$. The solid which gradually formed was collected and washed with large quantities of $H_2O$. This gave 0.66 g of off-white solid; 99.5% crude yield; mp 129°-235° L C. This crude product was then dissolved in hot isopropanol and acidified with dry HCl in absolute EtOH. The white precipitate was collected after chilling and washed with cold isopropanol to yield 0.48 g (68%) of the title compound after recrystallization from isopropanol, mp 225°-227° C.

EXAMPLE 5

Preparation of 7-[2-(benzoyloxy)-3-(isopropylamino)propoxy]flavone hydrochloride 7-[2-Hydroxy-3-(benzylisopropylamino)propoxy]flavone Following variation 1 of Method B, as outlined in Example 2, but substituting 7-(2,3-epoxypropoxy)flavone for 8-(2,3-epoxypropoxy)flavone, the title compound was prepared in 64% yield, m.p. 190°-191° C. (MeOH/Ether).

7-[2-(Benzoyloxy)-3-(isopropylamino)propoxy]flavone hydrochloride

Following Method D, step 1, as outlined in Example 1, but substituting 7-[2-hydroxy-3-(benzylisopropylamino)propoxy]flavone for 7-[2-hydroxy-3-[N-(benzyloxycarbonyl)-propylamino]propoxy]flavone, substituting benzoyl chloride for diphenylacetyl chloride, and deleting the HPLC step resulted in the formation of the product of 7-[2-(benzoyloxy)-3-(benzylisopropylamino)propoxy]flavone, in crude form. The product was hydrogenated according to Method D, step two, as outlined in Example 1, giving the title compound in 39% yield, m.p. 216°-218° C. (i-PrOH-MeOH).

EXAMPLE 6

Preparation of 7-[2-(Diphenylacetoxy)-3-(benzylisopropylamino)-propoxy]flavone hydrochloride Following steps 1 and 2 of Method D, as outlined in Example 1, but substituting 7-[2-hydroxy-3-(benzylisopropylamino)propoxy]flavone for 7-[2-hydroxy-3-[N-(benzyloxycarbonyl)-propylamino]propoxy]flavone, the title compound (m.p. 164°-166°) was obtained (step 1, 66% yield; step 2, 97% yield).

EXAMPLE 7

Preparation of 7-[2-(Diphenylacetoxy)-3-(isopropylamino)-propoxy]-flavone maleate 7-[2-(Diphenylacetoxy)-3-(benzylisopropylamino)-propoxy]flavone was prepared as in Example 5. Following step 2 of Method D, as outlined in Example 1, but substituting 7-[2-(diphenylacetoxy)-3-(benzylisopropylamino)propoxy]flavone for 7-[2-(diphenylacetoxy)-3-[N-(benzyloxycarbonyl)-propylamino]propoxy]flavone, and acidifying with maleic acid instead of HCl, the title compound was produced in 52% yield, m.p. 182°-183°.

EXAMPLE 8

Preparation of 8-[2-Hydroxy-3-(isopropylamino)propoxy]flavone hydrochloride

Following variation 2 of Method B, as outlined in Example 1, but substituting isopropylamine for n-propylamine and 8-(2,3-epoxypropoxy)flavone for 7-(2,3-epoxypropoxy)flavone, the title compound was prepared in 30% yield, m.p. 225°-227° C. (MeOH).

EXAMPLE 9

Preparation of 8-[2-Hydroxy-3-(propylamino)propoxy]flavone hydrochloride

8-[2-Hydroxy-3-(benzylpropylamino)propoxy]flavone

Following variation 1 of Method B, as outlined in Example 2, but substituting N-propyl-benzylamine for N-isopropyl-benzylamine, the title compound was prepared as a crude product (89% crude yield; m.p. 187°–192° C.).

8-[2-Hydroxy-3-(propylamino)propoxy]flavone hydrochloride

Using the step 2 Method D, as outlined in Example 1, the 8-[2-hydroxy-3-(benzylpropylamino)propoxy]flavone was converted into the title compound in 87% yield, m.p. 223°–224° C. (EtOH).

EXAMPLE 10

Preparation of 8-[2-(benzoyloxy-3-(propylamino)propoxy]flavone maleate

8-[2-(Benzoyloxy)-3-(benzylpropylamino)propoxy]flavone hydrochloride

Following step 1 of Method D, as outlined in Example 1, but substituting 8-[2-hydroxy-3-(benzylpropylamino)propoxy]flavone for 7-[2-hydroxy-3-[N-(benzyloxycarbonyl)-propylamino]propoxy]flavone, and benzoyl chloride for diphenylacetyl chloride, the title compound was formed in 78% yield.

8-[2-(Benzoyloxy)-3-(propylamino)propoxy]flavone hydrochloride

Following step 2 of Method D as outlined in Example 1, 8-[2-(benzoyloxy)-3-(benzylpropylamino)propoxy]flavone hydrochloride was converted to the title compound.

8-[2-(Benzoyloxy)-3-(propylamino)propoxy]flavone Maleate

This maleate was formed (m.p. 175°–176° C.; 90% yield) from the 8-[2-(benzoyloxy)-3-(propylamino)propoxy]flavone hydrochloride by base treatment and isolation of the free base which was then converted to the maleate salt by treatment with maleic acid.

EXAMPLE 11

Preparation of 8-[2-(diphenylacetoxy)-3-(propylamino)propoxy]flavone hydrochloride

8-[2-(Diphenylacetoxy)-3-(benzylpropylamino)propoxy]flavone hydrochloride

Following step 1 of Method D, as outlined in Example 1, but substituting 8-[2-hydroxy-3-(benzylpropylamino)propoxy]flavone for 7-[2-hydroxy-3-[N-benzyloxycarbonyl)-propylamino]propoxy], the title compound was prepared as an oil (52% purified yield).

8-[2-(Diphenylacetoxy)-3-(propylamino)propoxy]flavone hydrochloride

Following step 2 of Method D, as outlined in Example 1, 8-[2-(diphenylacetoxy)-3-(benzylpropylamino)propoxy]flavone was converted to the title compound as a white solid, m.p. 123°–125° C. (EtOH); 27% yield.

EXAMPLE 12

Preparation of 8-[2-(pivaloyloxy)-3-(benzylpropylamino)propoxy]flavone hydrochloride by Method D, Step 1

A solution of 8-[2-hydroxy-3-(benzylpropylamino)-propoxy]flavone hydrochloride (0.67 g, 1.4 mmol), pivaloyl anhydride (1.7 g, 9.2 mmol), 4-(dimethylamino)-pyridine (0.05 g, 0.4 mmol), triethylamine (3.1 ml, 11.2 mmol), and methylene chloride (30 ml) was heated at reflux, in the presence of nitrogen, for three days. The solvents were evaporated. The residue was taken up in methylene chloride, washed twice with saturated aqueous sodium bicarbonate, once with water, and dried ($Na_2SO_4$). Evaporation of the dried solution gave 2.23 g of yellow oil. The crude material was purified by flash chromatography, eluting initially with 3%, then 5% acetone in methylene chloride, and finally 5% MeOH in methylene chloride with a trace of ammonium hydroxide. This gave 1.09 g of yellow oil. The oil was dissolved in hot abs. ethanol, acidified with saturated hydrogen chloride in ethanol, and then diluted with ether. The precipitate was collected by filtration, and washed with cold ethanol/ether to give the title compound as a white solid (0.60 g, 72% yield), m.p. 172°–174° C. (MeOH-Ether).

EXAMPLE 13

Preparation of 8-[2-(Pivaloyloxy)-3-(propylamino)propoxy]flavone hydrochloride Employing the step 2 of Method D as outlined in Example 1, the title compound was prepared from 8-[2-(pivaloyloxy)-3-(benzylpropylamino)propoxy]flavone hydrochloride in 46% yield, m.p. 189°–191° C. (EtOH-Ether).

The preparation of the compounds of the invention may be further illustrated as follows:

By following Step 1 of Method D, as outlined in Example 1, but substituting
3-phenylpropionyl chloride (3-propylphenyl)acetyl chloride,
(2-chloro-4-ethoxyphenyl)acetyl chloride, or n-butyryl chloride for diphenylacetyl chloride will result in
7-[2-(3-phenylpropionyloxy)-3-[N-(benzyloxycarbonyl)-propylamino]propoxy]flavone,
7-[2-[(3-propylphenyl)acetoxy]-3-[N-(benzyloxycarbonyl)-propylamino]propoxy]flavone,
7-[2-[2-chloro-4-ethoxyphenyl)acetoxy]-3-[N-(benzyloxycarbonyl)-propylamino]propoxy]flavone, or
7-[2-(butyryloxy)-3-[N-(benzyloxycarbonyl)-propylamino]propoxy]flavone, respectively, instead of 7-[2-(diphenylacetoxy)-3[N-(benzyloxycarbonyl)-propylamino]propoxy]flavone.

By following Step 2 of Method D, as outlined in Example 1, but subtituting
7-[2-(3-phenylpropionyloxy)-3-[N-(benzyloxycarbonyl)-propylamino]propoxy]flavone,
7-[2-[(3-propylphenyl)acetoxy]-3-[N-(benzyloxycarbonyl)-propylamino]propoxy]flavone,
7-[2-[2-chloro-4-ethoxyphenyl)acetoxy]-3-[N-(benzyloxycarbonyl)-propylamino]propoxy]flavone, or
7-[2-(butyryloxy)-3-[N-(benzyloxycarbonyl)-propylamino]propoxy]flavone, respectively, for 7-[2-(diphenylacetoxy)-3[N-benzyloxycarbonyl)-propylamino]propoxy]flavone will result in 7-[2-(3-phenylpropionyloxy)-3-(propylamino)propoxy]-flavone, 7-[2-[(3-propylphenyl)acetoxy]-3-(propylamino)-propoxy]flavone, 7-[2-[(2-chloro-4-ethoxyphenyl)acetoxy]-3-(propylamino)propoxy]flavone, or 7-[2-(butyryloxy)-3-(propylamino)propoxy]flavone, respectively, instead of 7-[2-(diphenylacetoxy)-3-(propylamino)propoxy]flavone.

By following Step 1 of Method D, as oulined in Example 1, but substituting
5-[2-hydroxy-3-[N-(benzyloxycarbonyl)-propylamino]-propoxy]flavone or
6-[2-hydroxy-3-[N-(benzyloxycarbonyl)-propylamino]-propoxy]flavone for
7-[2-hydroxy-3-[N-(benzyloxycarbonyl)-propylamino]-propoxy]flavone, results in
5-[2-(diphenylacetoxy)-3-[N-(benzyloxycarbonyl)-propylamino]propoxy]flavone or
6-[2-(diphenylacetoxy)-3-[N-(benzyloxycarbonyl)-propylamino]propoxy]flavone, respectively, instead of
7-[2-(diphenylacetoxy)-3-[N-(benzyloxycarbonyl)-propylamino]propoxy]flavone By following Step 2 of Method D, as outlined in Example 1, but substituting
5-[2-(diphenylacetoxy)-3-[N-(benzyloxycarbonyl)-propylamino]propoxy]flavone or
6-[2-(diphenylacetoxy)-3-[N-(benzyloxycarbonyl)-propylamino]propoxy]flavone for
7-[2-(diphenylacetoxy)-3-N-(benzyloxycarbonyl)-propylamino]propoxy]flavone, results in
5-[2-(diphenylacetoxy)-3-(propylamino)propoxy]flavone or
6-[2-(diphenylacetoxy)-3-(propylamio)propoxy]flavone, respectively, instead of
7-[2-(diphenylacetoxy)-3-(propylamino)propoxy]flavone.

Alternative Conditions for Synthesizing the Compounds

Instead of using Method A, as exemplified above, to accomplish the first step in Chart A, it may be preferable to use another procedure that has been relatively successful in the synthesis of 7-(2,3-epoxypropoxy)flavone. This procedure is exemplified as follows:

20.0 g (0.084 mol) 7-hydroxyflavone was mixed with 350 ml acetonitrile followed by the addition of 77.7 g (0.84 mol) epichlorohydrin and 23.2 g (0.168 mol=2.0 x) potassium carbonate followed by heating at 75° for 16 hr with brisk stirring. The hot reaction mixture was filtered and the solid rinsed with 50 ml warm acetonitrile. The clear light yellow filtrate was concentrated under reduced pressure to a semisolid residue which was slurried with 100–150 ml isopropyl alcohol. (and collected with the aid of a 50 ml isopropyl alcohol rinse). The off-white solid was air dried followed by vacuum at 50°; yield 21.5 g (0.073 mol) 87.0%; m.p. 126°–129°.

Instead of using Method B, variation 2, as exemplified above, to accomplish the synthesis of a 5-, 6-, 7- or 8-(3-alkylamino-2-hydroxypropoxy)flavone maleate, it may be preferable to use another procedure that has been relatively successful in the synthesis of 7-(3-propylamino-2-hydroxypropoxy)flavone maleate. This procedure is exemplified as follows:

200 ml absolute ethanol was mixed with 400 ml n-propylamine (4.87 mol) and the resulting warm solution was cooled to 10° followed by the addition, in portions, of 21.5 g (0.073 mol) 7-(2,3-epoxypropoxy)flavone. The mixture was heated to 50°–55° for 1.5 h with stirring to give a deep yellow solution which was then cooled, concentrated under reduced pressure, and vacuum dried. The resultant yellow solid, consisting of ca. 1:1 free base of product and ring open chalcone, was dissolved in 300 ml warn absolute ethanol containing 42.3 g (0.365 mol) maleic acid and heated at 60° for 2 h after which time no chalcone remained. Slow-cooling, with stirring, with final cooling at 10°–15° for 0.5 h produced off-white crystals which were collected, rinsed with 50 ml cool (10°) ethanol, the vacuum dried at 70°; yield 31.2 g (0.0665 mol) 91.0%, 79.1% overall.

The crude maleate was dissolved, by slight warming, in 450 ml $H_2O$ and 150 ml 95% ethanol. (The crude maleate was then submitted to acid-base extractive work up to remove trace impurities). This solution was acidified to pH 1-2 with 60 ml 2.5N HCl and, after cooling to ambient temperature, extracted with three 50 ml portions of $CH_2Cl_2$. Slow addition, with stirring, of 2.5N NaOH into the aqueous layer to pH-11 produced a white solid which was stirred several hours to ensure complete precipitation. The white solid was collected, rinsed with two 100 ml $H_2O$ portions (filtrate pH 9) air dried several hours, then vacuum dried at 50° to a constant weight of 22.0 g (0.0622 mol); 93.7% conversion.

A solution of the free base, dissolved by warming, in 400 ml absolute ethanol containing 7.94 g (0.0685 mol×1.1 X) maleic acid was heated to boiling, filtered and slowly cooled with stirring for 2 h. The crystalline white product was collected, rinsed with two 50 ml portions of cool (10°) absolute ethanol, air dried, then vacuum dried at 70°; yield 27.0 g (0.0575 mol) 86.6% conversion, 68.4% overall. The maleate was recrystallized in 500 ml absolute ethanol, collected, and dried as above; yield 25.0 g (0.0532 mol) 80.1% conversion from crude maleate, 72.9% from epoxide, 63.4% overall from 7-hydroxyflavone; snow white crystals, m.p. 172.0°–173.0°.

Antiarrhythmic Activity

Antiarrythmic activity of a compound of the invention can be demonstrated in anesthetized dogs in which arrythmia had been induced by administration of ouabain:

Ouabain can be prepared as a 0.1% (1 mg/ml) solution in 0.9% saline. A hot tap water bath and stirring of the solution facilitate preparation.

A. Experimental Procedure. Dysrhythmias are induced by consecutive injections of ouabain. A primary dose of ouabain, 50 μg/kg, is injected. At 15 minute intervals thereafter, 10 μg/kg is injected until the appearance of either (a) ventricular tachycardia or (b) ectopic dysrhythmias (uni- or multifocal). If a dysrhythmia appears, and reverts spontaneously, an additional 5 μg/kg of ouabain may be administered, repeated 15 minutes later, if necessary. The total cumulative dose of ouabain necessary to induce dysrhythmias ranges from 60 to 130 μg/kg. Frequent monitoring of the ECG is necessary to observe the changes induced by ouabain. Once a suitable dysrhythmia has been established the dysrhythmia is allowed to continue for 15 minutes. The test compound is then injected i.v., usually at 1 mg/kg. Observe the ECG for 5 to 10 minutes. If the dysrhythmia is altered, or reversed to a sinus pattern, wait until the dysrhythmia reappears. Then, if additional data is desired, inject a higher dose of test compound, such as 3 mg/kg. In this manner, progressively larger doses (as high as 30 mg/kg, for example) may be tested on the same dog. [If, during the sequential testing, dysrhythmia does not reappear within about an hour of its disappearance, an additional dose of ouabain, such as 5 µg/kg, may be administered to reinduce it.] In any case, once the final dose has been tested, dysrhythmia is allowed to reappear and the validation procedure is performed. The required dose to reverse dysrhythmia will not only depend on which compound is being tested, it will to some extent depend on the individual dog tested.

If the initial dose of a compound does not alter dysrhythmia, successively higher doses may be tested. If no dose results in a reversal of dysrhythmia, the validation procedure should be performed.

1. Inactive Compound: The test compound does not alter or reverse the induced arrhythmias.
2. Active Compound:
A. A normal ECG (relative to control) is established.
B. The appearance of a sinus rhythm (p waves precede each ventricular cycle, indicating return of the normal conduction pattern).

Validation Procedure:

If the dysrhythmia has not been reversed by the test compound, or reappears after being reversed by the test compound, a positive control should be obtained. Two anti-dysrhythmic agents, lidocaine HCl and procainamide, are used. Generally, 1 mg/kg lidocaine HCl i.v. reverses the dysrhythmia. If 1 mg/kg lidocaine HCl is ineffective, administer 2 mg/kg. If that treatment is ineffective, administer 10 mg/kg procainamide i.v., and if necessary, 20 mg/kg. If reversal of the dysrhythmia to a sinus pattern is not obtained subsequent to treatment with either drug, the test is considered invalid.

Preferred Compound:

The preferred compound is considered to be 7-[2-(diphenylacetoxy)-3-(isopropylamino)propoxy]flavone maleate as regards antidysrhythmic activity.

EXAMPLE 14

In a dog in which dysrhythmia had been induced by 70 µg/kg of ouabain by the above procedure, antidysrhythmic activity was observed after each of the following sequentially injected doses of 7-[2-(diphenylacetoxy)-3-(isopropylamino)propoxy]flavone: 1 mg/kg and 3 mg/kg.

Other Mammals

The compounds of the invention can be used as antiarrhythmic agents in other mammals, including humans, using the effective dosage in dogs as a starting point for dosage estimates. Nevertheless, well established principles of experimental medicine dictate that the effective dose for a given compound in a given human requires titration of the dosage in that human to obtain maximum efficiency while minimizing undesirable side effects. Preferred routes of administration of the drug are the intravenous and oral ones. Intramuscular and subcutaneous administration is also possible.

What is claimed is:

1. A compound of the formula

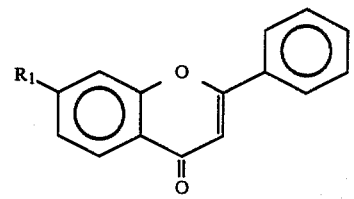

or a pharmaceutically acceptable salt thereof wherein $R_1$ is

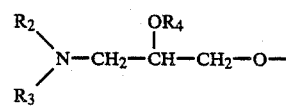

$R_2$ is n-propyl or i-propyl,
$R_3$ is hydrogen, and
$R_4$ is benzoyl or diphenylacetyl and is benzoyl only when $R_2$ is i-propyl.

2. A compound according to claim 1 wherein $R_2$ is n-propyl and $R_4$ is diphenylacetyl.
3. A compound according to claim 1 wherein $R_2$ is i-propyl and $R_4$ is diphenylacetyl.
4. A compound according to claim 1 wherein $R_2$ is i-propyl and $R_4$ is benzoyl.
5. A compound of the formula

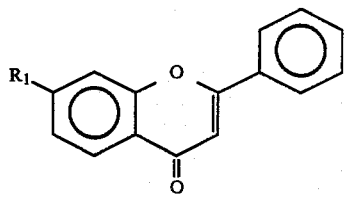

or a pharmaceutically acceptable salt thereof wherein $R_1$ is

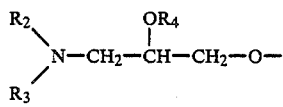

$R_2$ is i-propyl,
$R_3$ is benzyl, and
$R_4$ is diphenylacetyl.
6. A compound of the formula

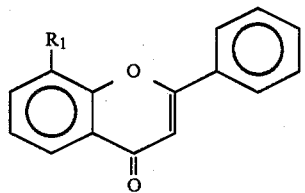

or a pharmaceutically acceptable salt thereof wherein $R_1$ is

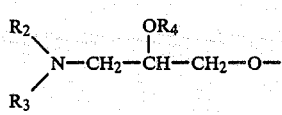

$R_2$ is t-butyl or n-propyl, $R_3$ is H, and $R_4$ is benzoyl.

7. A compound according to claim 6 wherein $R_2$ is t-butyl.

8. A compound according to claim 6 wherein $R_2$ is n-propyl.

9. A compound of the formula

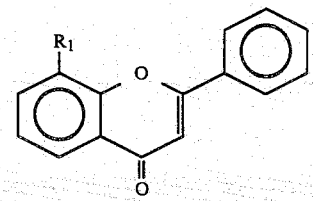

or a pharmaceutically acceptable salt thereof wherein $R_1$ is

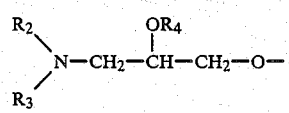

$R_2$ is n-propyl,
$R_3$ is hydrogen or benzyl, and
$R_4$ is pivaloyl.

10. A compound according to claim 9 wherein $R_3$ is hydrogen.

11. A compound according to claim 9 wherein $R_3$ is benzyl.

* * * * *